(12) United States Patent
Simpson et al.

(10) Patent No.: US 7,525,658 B1
(45) Date of Patent: Apr. 28, 2009

(54) SYSTEM OF CORRELATING LIGHT MEASUREMENTS

(75) Inventors: Jeffrey A. Simpson, Wayne, NE (US); Mark A. Imbrock, Sylvania, OH (US); Nathan Strimpel, Carleton, MI (US)

(73) Assignee: Electronic Design To Market, Inc., Toledo, OH (US)

( * ) Notice: Subject to any disclaimer, the term of this patent is extended or adjusted under 35 U.S.C. 154(b) by 498 days.

(21) Appl. No.: 11/504,347

(22) Filed: Aug. 15, 2006

Related U.S. Application Data

(60) Provisional application No. 60/708,146, filed on Aug. 15, 2005.

(51) Int. Cl.
*G01B 11/00* (2006.01)
*G01N 21/00* (2006.01)

(52) U.S. Cl. ................................. 356/394; 356/432

(58) Field of Classification Search .................. None
See application file for complete search history.

(56) References Cited

U.S. PATENT DOCUMENTS

2002/0067489 A1* 6/2002 Thakur et al. ............... 356/600

* cited by examiner

*Primary Examiner*—Gregory J Toatley, Jr.
*Assistant Examiner*—Amanda H Merlino
(74) *Attorney, Agent, or Firm*—MacMillan Sobanski & Todd, LLC

(57) ABSTRACT

A system provides a correlation between a field-tested measured light transmission, light reflection and/or light absorption in at least one transparent, translucent or semi-opaque medium to a pre-set measured light transmission.

20 Claims, 3 Drawing Sheets ively 45%. Also, a single pane window reduces UV energy by about 22-28% and a double pane window about 40%, while a high performance window can exceed an 80% reduction.

SYSTEM OF CORRELATING LIGHT MEASUREMENTS

REFERENCE TO RELATED APPLICATIONS

This application claims the benefit of U.S. Provisional Application No. 60/708,146, filed Aug. 15, 2005, the disclosure of which is expressly incorporated herein by reference.

TECHNICAL FIELD

The invention relates generally to a system of correlating measured light transmissions, reflections or absorptions in a transparent, translucent or semi-opaque medium.

BACKGROUND OF THE INVENTION

In the glass and window industry, customers who are contemplating the purchase of high quality and high performance windows want to be assured that the windows will meet their needs. For example, a single pane window transmits about 90% of the sun's energy, while a double pane window transmits about 45%. Also, a single pane window reduces UV energy by about 22-28% and a double pane window about 40%, while a high performance window can exceed an 80% reduction.

However, the window's performance characteristics, such as the amount of solar and UV transmission reduction, are invisible to the customer. In order to demonstrate the window's effectiveness, a sales associate will often use a portable light sensing meter and a portable light source to demonstrate the window's features.

Often, the light source used on the demonstration is a single light source (for example, a heat lamp or a UV "black" light) to mimic the light energy provided by the sun. However, these light sources have limited light spectrum that is not as broad as the natural sunlight spectrum. That is, the light source from such products does not provide energy across the entire light spectrum.

Also, the portable light meters have a limited range of sensitivity. That is, the light sensor in the meter does not have a "flat" or "the same" response for every wavelength across the entire light spectrum. When the light sources are used with the portable light meters, the meters do not always accurately produce a transmission measurement that is the same as the window manufacturer's "laboratory-tested" specifications.

The manufacturer's laboratory-tested specifications are typically the result of highly sophisticated testing using expensive and highly accurate equipment. In the industry, many laboratory measurements are performed using a spectrometer that has a light source over the whole spectrum and a prism to break down the spectrum to provide a transmission percentage to each wavelength. The percentages then can be averaged together to give a total transmission for a given spectrum (for example, solar, UV, visible). Mathematical calculations are performed which allow the user to select certain light frequency ranges. Then, individual wavelength measurements can be made on each uniquely defined light sensing pixel or element, and the resulting summation of the data can be made in the laboratory. Unfortunately, this type of equipment is either unavailable or impractical to use in the commercial or sales environment.

Therefore, the results from a limited range light source and a limited range sensor are used as the "true" or "field-tested" transmission performance of a broader light spectrum. There is generally no correlation, however, between the "laboratory-tested" measurements and the "field-tested" measurements. This poses a problem since the customer is expecting to see the same "laboratory-tested" measurements that are set forth in the window manufacturer's specifications.

In one example, the common practice among window industries' sale presentations is to use a solar meter in conjunction with a heat lamp to demonstrate the percentage of solar energy blocked by their product. The sensor in the meter has limited range, as shown in FIG. 1, and has a highly nonlinear output over the light wavelength range that the sensor can measure. The common heat lamp has a defined light frequency range, as shown in FIG. 2.

Glass manufacturers generally list the percentage of solar transmission based on the entire solar energy range. The solar spectrum is shown in FIG. 3. However, due to the above-described limitations of the heat lamp and the limitations of sensor technology available, the existing meter's transmission measurements do not equal the manufacturer's data sheets.

Thus, there exists a need for an efficient system for correlating field-tested measurement with the manufacturer's stated laboratory-tested measurements.

SUMMARY

In one aspect, a method is provided for correlating a field-tested measurement and a pre-set measurement of light in a transparent, translucent or semi-opaque medium. The method includes transmitting light from a source through a medium to be tested, where the transmitted light has desired properties; sensing the desired light property with a light sensor to obtain a field-tested measurement; correlating the field-tested measurement to a pre-set measurement; and, generating a final result output signal which is the result of a correlation between the field-tested measurement and the pre-set measurement. The light being measured can be in one or more of UV, visible or infrared spectral ranges.

In another aspect, a system, or apparatus, is provided for correlating measured light transmission, light reflection and/or light absorption in at least one transparent, translucent or semi-opaque medium. The system includes a light source for transmitting light through the medium, where the transmitted light has at least one desired property. At least one light sensor is configured to: i) sense the desired light property, ii) correlate the sensed light property to a pre-set measurement, and iii) generate an output signal that is substantially the same as the pre-set measurement.

Various objects and advantages of this invention will become apparent to those skilled in the art from the following detailed description of the preferred embodiment, when read in light of the accompanying drawings.

DETAILED DESCRIPTION OF THE INVENTION

Figure 1:
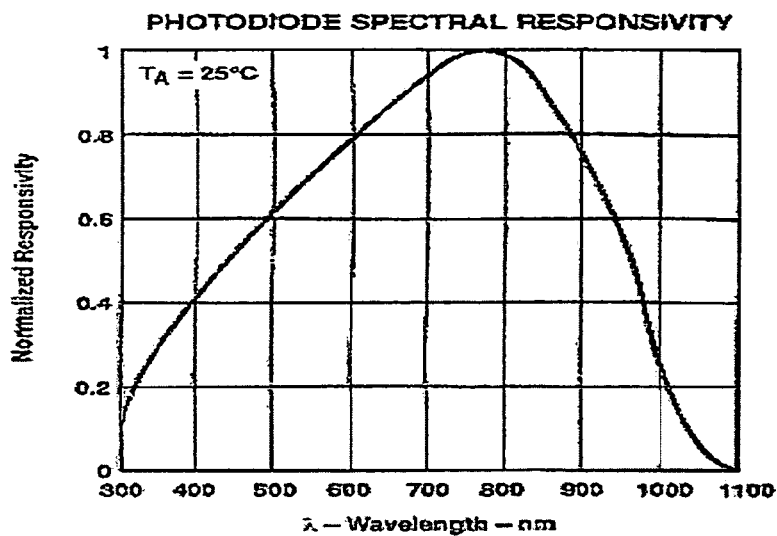
FIG. 1 is a graph illustrating that a sensor has limited range and a highly nonlinear output over the light wavelength range.
Figure 2:
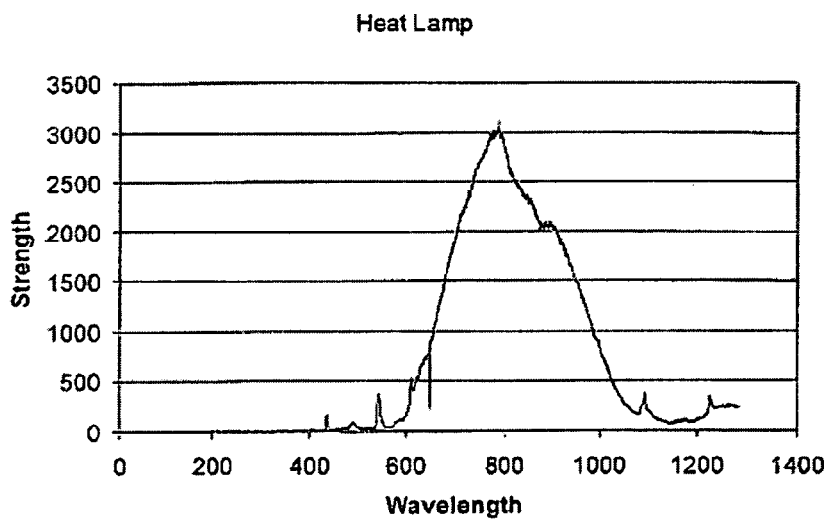
FIG. 2 is a graph illustrating that a common heat lamp has a defined light frequency range.
Figure 3:
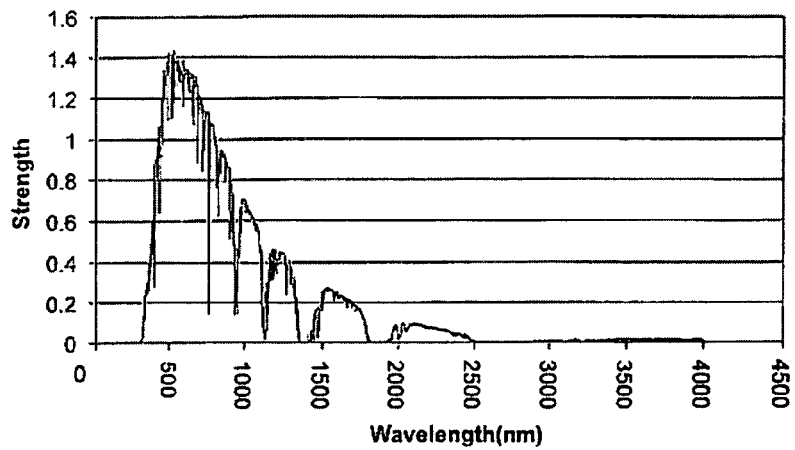
FIG. 3 is a graph illustrating the entire solar spectrum.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are described herein.

The light measurement correlation system can be applied to any specific light source and any given sensor. For ease of explanation, only the explanation of UV and visible light transmission measurements will be shown and described in detail herein. However, it should be understood that the system described herein is useful for various defined light ranges.

Also, for ease of explanation, only the explanation of light transmission measurements will be shown and described in detail herein. However, it should be understood that the system described herein also applies to light reflection and/or light absorption measurements.

The light measurement correlation system significantly improves the correlation between the factory pre-set (i.e., laboratory-tested) light transmission measurements and field-tested light transmission measurements.

The light measurement correlation system is useful to readily and accurately reflect the manufacturer's stated pre-set light transmission measurements through one or more transparent, translucent and semi-opaque media, either alone or in combination. Examples of such measurable media include, for example, but are not limited to one or more of: architectural windows with or without coatings or layers of light-altering materials; coated films on glass or plastics; glass such as automobile windows, adjustable darkness glass, user adjustable privacy glass, eyeglass lenses; plastics such as windows, storage containers; and, transparent metal layers such as those found in photovoltaic devices and solar panels.

Further, it is to be understood, that in certain other end-use applications, other light environments can be measured with the light measurement correlation system 10. In such end-use applications, the light sources and the light sensor are calibrated, or normalized to the particular light environment. Examples of such end use applications include, but are not limited to, a photopic environment (such as characterization of the human retina, vitreous humor, blood), or a solar-like environment (i.e., imitation of the sun).

The light measurement correlation system significantly improves light transmission measurements by correlating a sensor response from a limited spectrum light source(s) to a broader spectrum response. In certain embodiments, the light measurement correlation system provides an output signal that is the same as the window manufacturer's "laboratory-tested" specifications. In other embodiments, the single output signal substantially reflects the pre-set measurement.

One transmission measurement setup uses a single limited spectrum lamp and a single sensor. To obtain an accepted industry accuracy measurement in light transmission measurements, the field-tested reading or transmission measurement is corrected, or adjusted, using mathematical equations or predetermined values.

In certain instances, the predetermined values can be obtained from pre-existing generated values. The equations and/or pre-existing values are derived from laboratory tested transmission values of different types of industry glass samples from different manufacturers. For example, according to one embodiment of the light measurement correlation system, the transmission percentage values that have been generated from the testing known glass samples from a particular manufacturer are used. The light measurement correlation system includes a light sensor, or meter, that is configured to read and measure the percentage of light being transmitted through a medium to be tested. In certain embodiments, the sensor is calibrated to a particular manufacturer so that when a particular medium is field-tested, or measured, the sensor will show the manufacturer's laboratory-tested value. In that way, the customer is reassured that, even though the portable sensor and/or limited light source is being used, the manufacturer's product does, in fact, meet the stated percentages of light transmission.

In certain embodiments, the light measurement correlation system can be calibrated so that the sensor can be used to test more than one manufacturer's product. For example, if one manufacturer's light transmission value is 24 and a second manufacturer's light transmission value is 20, the sensor of the light transmission correlation system can be calibrated to show a best approximation, or extrapolation, by showing an average value, i.e., 22. The transmission percentage values are thus correlated so that, when the light transmission correlation system tests media products from different manufacturers, the customer can be assured that the displayed output signal showing the best approximation is a generally accurate indication of the product's light transmission values.

Figure 4:
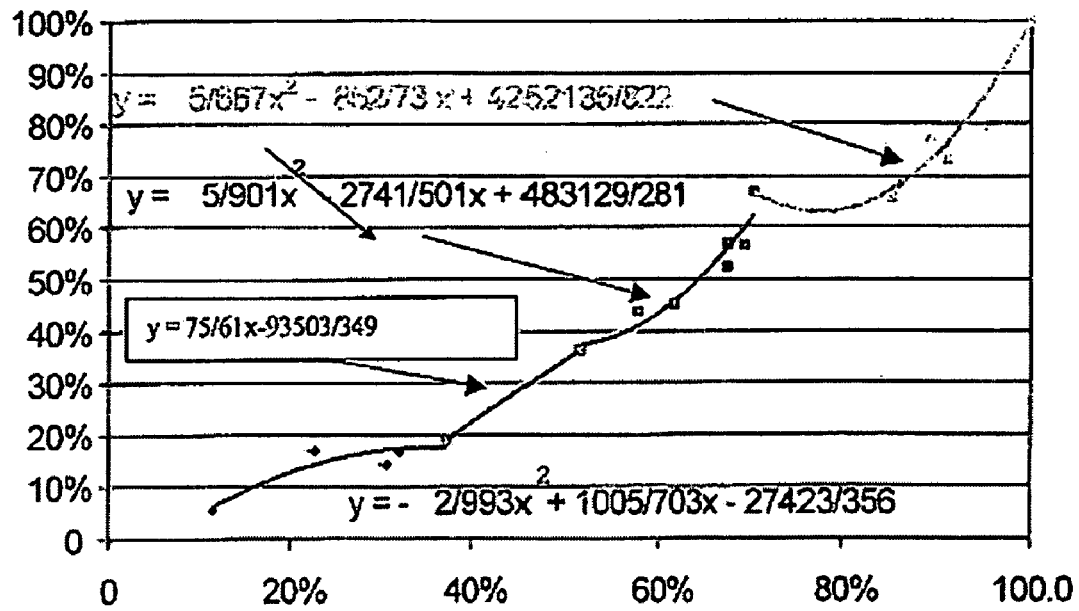
FIG. 4 is a graph illustrating UV transmission corrections.
Figure 5:
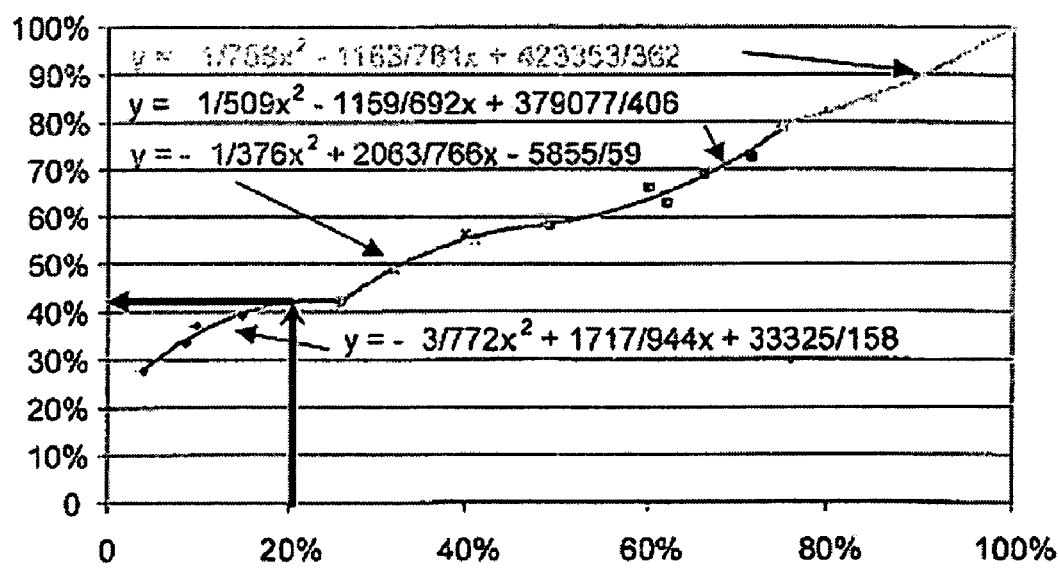
FIG. 5 is a graph illustrating solar transmission corrections.

FIGS. 4 and 5 are graphs illustrating the correlation between the actual transmission results of a commonly used light source and a commonly used light sensor using a polynomial equation which provides a match to industry accepted light transmission measurements. FIG. 4 shows the UV spectrum corrections and FIG. 5 shows the Solar transmission corrections. Note in FIG. 5 a common heat lamp and sensor transmission measurement provides results of approximately 22%. Upon applying the correct polynomial equation, the accepted industry measurement of 43% is correctly obtained.

The light transmission correlation system method improves the accuracy of field tests of light transmission measurements by correlating i) the response of one or more sensors from one or more limited spectrum light sources, to ii) a broader spectrum response, i.e., a highly accurate, or laboratory-tested measurement. One or more equations may be used to correlate specific light transmission spectrum measurements to industry-accepted values of a defined light range.

In certain embodiments, the correlation is empirically generated and entered into the sensor. For example, the correlation between the field-tested measurement and the laboratory measurement can be determined by using one or more correlation tables and/or one or more equations. The correlation tables contain data that have been generated through testing of individual types of media. One or more correlation tables may be used to correlate specific light spectrums to industry-accepted values for defined transmission range measurements.

Two or more light sources may be used in a defined sequence or simultaneously with two or more sensors to provide results that are applied to mathematical equations or to look up tables to achieve industry accepted values.

A specific range of a sensor may also be used alone or in conjunction with another sensor to provide a correlation.

Figure 6:
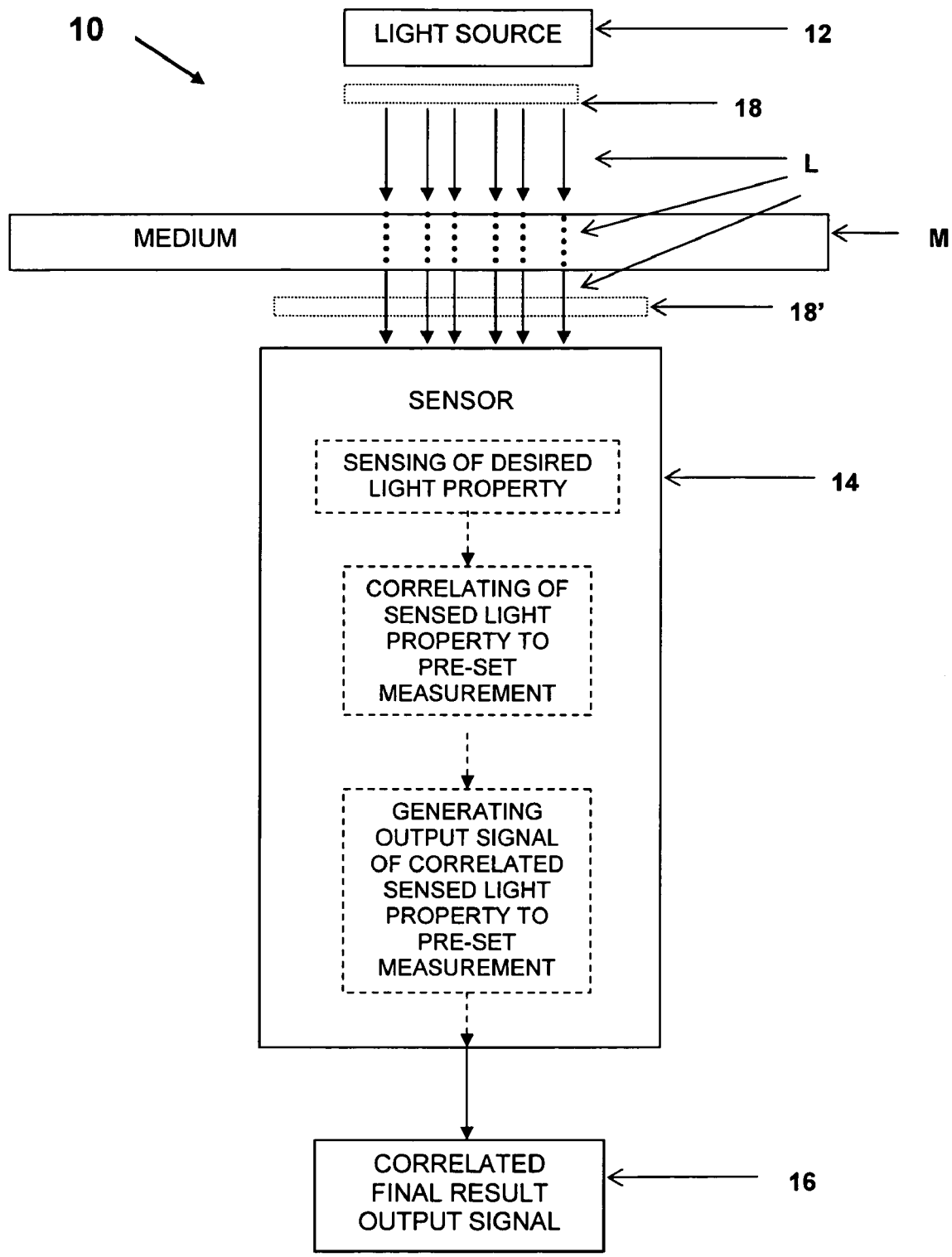
FIG. 6 is a schematic illustration of a light measurement correlation system.

A light transmission, reflection or absorption instrument may be integrated with the above methodology of mathematical equations or lookup tables to improve the accuracy of light transmission measurements FIG. 6 schematically illustrates a light measurement correlation system 10 having a discrete light source 12 and at least one light sensor 14. The light source 12 is combined, or aligned, with the light sensor 14 such that the light L passes through a medium M being tested. For ease of illustration, the light L is shown as being transmitted through a medium M that is transparent, translucent or semi-opaque; however, as discussed herein, the light measurement correlation system 10 can be used to detect reflection and/or absorption as well as transmission of light through the medium M.

The light sensor 14 can be operatively connected to an output signal device 16 that provides a final result "FR" (also referred to herein as "field-tested" or "final result" or "output signal").

Any suitable non-linear (or linear) light sensor 14 that is capable of detecting wavelengths of light may be used. Also, in certain embodiments, one or more optical altering devices 18 and 18', such as filters, beam-splitters, lenses and the like, can be used on the light source 12, the light sensor 14, or both. For example, an optical filter may be used to change the light frequency characteristics of the light source 12 or the non-linear light sensor 14 in the light measurement correlation system 10. The change in response to the individual light frequency characteristics may allow for easier system matching in order to generate the final result output signal from the defined light environment.

It is to be noted that while light sensors 14 are understood to have a non-flat (non-linear) spectral response over a range of light frequencies, the light measurement correlation system 10 generates an overall industry tested spectral response (i.e., the "final-result" single output signal).

It is to be understood that various suitable algorithms or mathematical techniques for generating and/or processing the final result output signal can be used. Further, the light measurement correlation system may be controlled and/or operated by conventional control and/or operational systems, including, but not limited to various software instructions and/or programs. It is to be understood that such instructions and programs are readily available to, or readily programmable, without undue experimentation from the descriptions as provided herein.

In certain embodiments, the light measurement correlation system 10 is used to create a specified light environment for the medium M under test by positioning the light source 12 and the sensor 14 on opposite sides of the medium M for sensing or measuring at least one of light transmission through, light reflection of, or light absorption by, the medium M.

In other embodiments, the light measurement correlation system 10 is used to create a specified light environment by positioning the light source 12 and the sensor 14 on a single side of the medium M for sensing or measuring at least one of light transmission through, light absorption by, or light reflection of, the medium M.

Also, in certain embodiments, the light measurement correlation system comprises multiple light sources and one light sensor. In certain embodiments, the light source and the light sensor comprise a single unit that is configured to be removably mounted against opposite sides of the medium. In other embodiments, the light source and the light sensor are separate elements that are configured to be removably mounted against opposite sides of the medium. In still other embodiments, the light measurement correlation system comprises a single unit having the light source and the light sensor that is configured to be mounted to one side of the medium for reflection measurements.

Also, in certain embodiments, the light measurement correlation system is configured to compensate for ambient conditions where the ambient conditions are also measured. The light measurement correlation system provides an adjusted final result signal to remove the effects of the ambient conditions.

While the invention has been described with reference to a preferred embodiment, it should be understood by those skilled in the art that various changes may be made and equivalents may be substituted for elements thereof without departing from the essential scope of the invention. In addition, many modifications may be made to adapt a particular situation or panel to the teachings of the invention without departing from the essential scope thereof, such as, for example, using UV, visible and infrared light or any other defined range. Therefore, it is intended that the invention not be limited to the particular embodiment disclosed as the best mode contemplated for carrying out this invention, but that the invention will include all embodiments falling within the scope of the claims.

What is claimed is:

1. A method for providing a correlation between a field-tested light measurement and a pre-set light measurement in a transparent, translucent or semi-opaque medium, comprising:
    transmitting light from at least one source at or through the medium, the transmitted light having at least one desired property;
    sensing at least one of the desired light properties with a light sensor to obtain a field-tested measurement;
    correlating the field-tested measurement to a pre-set measurement; and,
    generating a final result output signal showing the correlation between the field-tested measurement and the pre-set measurement, wherein the correlation includes correlating a limited range light spectrum to a broader light spectrum.

2. The method of claim 1, wherein the light is in at least one of UV, visible or infrared spectral ranges.

3. The method of claim 1, wherein the light property sensed is one of light transmission, light reflection or light absorption.

4. The method of claim 1, wherein the final result output signal substantially reflects the pre-set measurement.

5. The method of claim 1, wherein one or more optical altering devices are used to change at least one performance characteristic of the light sensor, the light source, or both.

6. The method of claim 1, further wherein the optical altering device comprises one or more of an optical filter, beam splitter, or lens.

7. The method of claim 1, wherein a created specified light environment for the medium is generated by positioning the light source and the sensor on opposite sides of the medium for sensing or measuring at least one of light transmission through, light reflection of, or light absorption by, the medium.

8. The method of claim 1, wherein a created specified light environment for the medium is generated by positioning the light source and the sensor on a single side of the medium for sensing or measuring at least one of light transmission through, light absorption by, or light reflection of, the medium.

9. The method of claim 2, wherein ambient conditions of the system are measured and the final resulting signal is adjusted to remove the effects thereof.

10. The method of claim 1, wherein the medium comprises one or more of glass, plastics, metals, fluids and gaseous environments.

11. The method of claim 1, wherein the medium comprises one or more of:
    architectural windows with or without coatings or layers of light-altering materials; coated glass; automobile windows; adjustable darkness glass; user adjustable privacy glass; eyeglass lenses; transparent metal layers including those found in photovoltaic devices and solar panels; fluids including human retina, vitreous humor, blood.

12. A system for correlating a field-tested light measurement in at least one transparent, translucent or semi-opaque medium to a pre-set measured light transmission, the system comprising:
   at least one light source configured to transmit light at or through the medium, the transmitted light having at least one desired property; and,
   at least one light sensor configured to: i) sense the desired light property to obtain a field-tested measurement, ii) correlate the sensed light property to a pre-set measurement, wherein the correlation includes correlating a limited range light spectrum to a broader light spectrum, and iii) generate an output signal.

13. The system of claim 12, wherein the light is in at least one of UV, visible or infrared spectral ranges.

14. The system of claim 12, wherein the light property sensed is one of light transmission, light reflection or light absorption.

15. The system of claim 12, wherein the single output substantially reflects the pre-set measurement.

16. The system of claim 12, wherein one or more optical altering devices are used to change at least one performance characteristic of the light sensor, the light source, or both.

17. The system of claim 16, further wherein the optical altering device comprises one or more of an optical filter, beam splitter, or lens.

18. The system of claim 12, wherein ambient conditions of the system are measured and the final resulting signal is adjusted to remove the effects thereof.

19. The system of claim 12, wherein the medium comprises one or more of glass, plastics, metals, fluids and gaseous environments.

20. The system of claim 12, wherein the medium comprises one or more of: architectural windows with or without coatings or layers of light-altering materials; coated glass; automobile windows; adjustable darkness glass; user adjustable privacy glass; eyeglass lenses; transparent metal layers including those found in photovoltaic devices and solar panels; fluids including human retina, vitreous humor, blood.

* * * * *